United States Patent
Hakky et al.

(10) Patent No.: US 9,498,596 B1
(45) Date of Patent: *Nov. 22, 2016

(54) CATHETER

(76) Inventors: Said I. Hakky, Largo, FL (US);
A-Hamid Hakki, Dunedin, FL (US)

(*) Notice: Subject to any disclaimer, the term of this patent is extended or adjusted under 35 U.S.C. 154(b) by 1069 days.

This patent is subject to a terminal disclaimer.

(21) Appl. No.: 13/433,818

(22) Filed: Mar. 29, 2012

Related U.S. Application Data (60) Continuation of application No. 13/369,372, filed on Feb. 9, 2012, which is a division of application No. 12/490,669, filed on Jun. 24, 2009, now Pat. No. 8,137,337.

(51) Int. Cl.
| | |
|---|---|
| *A61M 25/04* | (2006.01) |
| *A61M 39/00* | (2006.01) |
| *A61M 25/00* | (2006.01) |
| *A61M 25/09* | (2006.01) |
| *A61M 5/32* | (2006.01) |

(52) U.S. Cl.
CPC ..... *A61M 25/0017* (2013.01); *A61M 25/0074* (2013.01); *A61M 25/04* (2013.01); *A61M 25/0905* (2013.01); *A61M 5/3271* (2013.01); *A61M 5/3272* (2013.01); *A61M 2025/0079* (2013.01); *A61M 2025/09125* (2013.01)

(58) Field of Classification Search
CPC ............. A61M 25/0905; A61M 2025/09125; A61M 25/10; A61M 25/0017; A61M 25/04; A61M 25/0074; A61M 25/0075; A61M 2025/0079; A61M 25/09041; A61M 5/3271; A61M 5/3272
USPC ........ 604/544, 6.16, 19, 93.01, 103.03, 104, 604/105, 107, 164.01, 174, 264, 540, 541, 604/543; 600/29–31, 38–41; 128/885, 128/897–898; 606/201–202
See application file for complete search history.

(56) References Cited

U.S. PATENT DOCUMENTS

| | | | | | |
|---|---|---|---|---|---|
| 2,556,783 | A | * | 6/1951 | Wallace | A61B 17/22 604/105 |
| 2,649,092 | A | * | 8/1953 | Wallace | A61M 25/04 604/105 |
| 3,713,447 | A | * | 1/1973 | Adair | A61M 25/06 604/105 |
| 3,799,172 | A | * | 3/1974 | Szpur | A61M 25/04 604/105 |
| 5,171,223 | A | * | 12/1992 | Herzberg | A61B 1/00085 604/104 |
| 5,185,004 | A | * | 2/1993 | Lashinski | A61M 25/0136 600/434 |

(Continued)

FOREIGN PATENT DOCUMENTS

EP    1023882 A1    8/2000

OTHER PUBLICATIONS

International Search Report of PCT/US2009/050544 dated Aug. 24, 2010.

*Primary Examiner* — Adam Marcetich
(74) *Attorney, Agent, or Firm* — Rosenberg, Klein & Lee (57) ABSTRACT

A catheter with an improved retaining, activation and locking features is provided which is a safe device with reduced irritation and discomfort for a patient. The retaining mechanism positioned at the proximal end of the catheter assumes a "closed" position for introduction and removal of the catheter into and from the body cavity of a patient, and is transitioned into the "open" position when the catheter is positioned within the body cavity by mechanically manipulating the retaining mechanism through an activation mechanism having a piston member slideably displaceable within a cylinder housing member. A locking mechanism is included for maintaining the catheter in the "open" position.

12 Claims, 4 Drawing Sheets

(56) References Cited

U.S. PATENT DOCUMENTS

| | | | | |
|---|---|---|---|---|
| 5,403,288 A | * | 4/1995 | Stanners | A61M 5/347 604/110 |
| 5,429,612 A | * | 7/1995 | Berthier | A61M 5/3257 604/110 |
| 5,688,241 A | * | 11/1997 | Asbaghi | A61M 5/326 604/110 |
| 5,707,357 A | | 1/1998 | Mikhail et al. | |
| 7,306,586 B2 | | 12/2007 | Beaufore et al. | |
| 2003/0078546 A1 | * | 4/2003 | Jensen | A61M 5/3202 604/232 |
| 2004/0230158 A1 | * | 11/2004 | Malenchek | A61M 5/3272 604/110 |
| 2005/0101941 A1 | * | 5/2005 | Hakky | A61M 25/04 604/544 |
| 2006/0282044 A1 | * | 12/2006 | Mohammed | A61B 5/1444 604/192 |
| 2007/0078386 A1 | * | 4/2007 | Salazar | A61M 25/04 604/96.01 |
| 2008/0172042 A1 | | 7/2008 | House | |

* cited by examiner

CATHETER

REFERENCE TO RELATED APPLICATIONS

This patent application is a Continuation in Part Application of U.S. patent application Ser. No. 12/490,669 filed 24 Jun. 2009, now pending and of U.S. patent application Ser. No. 13/369,372 filed on 9 Feb. 2012, now pending.

FIELD OF THE INVENTION

The present invention relates to surgical devices. In particular, this invention relates to surgical systems directed to infusion and draining of fluids to and from a patient's body.

More in particular, this invention is directed to a catheter system having a retaining mechanism for maintaining the catheter in a relatively stable position within a body cavity of a patient.

Still further this invention is directed to a catheter system which includes a retaining mechanism which is selectively displaced to an "open" position within a patient's body cavity during a procedure to maintain relative stability within the patient's body. Additionally, this invention is directed to a catheter system which is selectively displaceable to a "closed" position for insert and removal of the catheter prior to and subsequent to a procedure.

More in particular, this invention is directed to an activation system which uses a piston to activate the retaining mechanism into the "open" or "closed" positions.

Still further, this invention is directed to a catheter system which includes a releasable locking mechanism to maintain the retaining mechanism in an "open" position during drainage, irrigation and/or medicinal delivery.

BACKGROUND OF THE INVENTION

Surgical devices directed to infusion and draining of fluids to and from a patient's body has been known for many years.

Initially, a catheter was developed known as the Foley catheter which incorporated a balloon-tipped retention urinary catheter. In this system, a balloon was provided with a drainage port as well as an infusion port. A proximal end of the catheter was provided and a side port was incorporated for inflation of the balloon. The balloon was inflated through some type of syringe which allowed passage of liquid through the side port. In this manner, the catheter was retained within a body cavity during a procedure. Since the Foley catheter was introduced, numerous types of catheter systems have been developed which permit retention of the catheter within the body cavity of a patient.

One of the important problems associated with catheters which are inserted into body cavities and retained therein during a procedure is the complexity of maintaining the retaining mechanism within the body cavity in a releasably locked condition.

A need has been developed to reduce the overall diameter of a catheter tubular member while maintaining a continuous flow passageway for either draining or infusion of liquids to and from the body cavity.

Complex mechanisms have been tried for releasably locking the retaining mechanism within the body cavity, however, such mechanisms generally are complex to operate and further (most importantly) take a large amount of manipulation which results in an extended time interval for the locking/unlocking procedure of the retaining mechanism. Such extended times are important especially when a patient is undergoing a procedure.

Subsequent to a catheter being positioned within the body cavity of a patient, the activation mechanism remains external to the patient's own body. A caregiver or other medical personnel manipulates the activation mechanism to transition the device between open and closed positions which correspond to the wings being in an extended position and in a flush position with respect to a flexible tubular member portion of the catheter.

Patients often will displace this portion of the catheter and such contact may cause the catheter to be unintentionally transitioned from the open to the closed position. This condition is especially true in cases where patients are catheterized but remain mobile.

Therefore, it is important for catheters to be equipped with a locking mechanism to protect against unintended transitioning while providing a locking mechanism which is easily manipulatable and reduces the time required for the caregiver to extend the retaining mechanism into the open position or the closed position.

Such locking mechanisms are important since it is critical that they be designed for use with the type of improved retaining mechanism as is herein described so that if the catheter is locked into its open position and subsequently removed from the patient's body cavity, the flexibility of the retaining mechanism will minimize tearing, rupturing, bleeding, and/or scarring to the lining of the patient's body cavity.

PRIOR ART

Prior art catheter systems for insertion and maintenance of the catheter within a body cavity of a patient are known in the art. Catheters having a retaining mechanism have been known since at least as early as the well-known Foley catheter which is a balloon-tipped retention urinary catheter. Originally, the Foley catheter was specifically directed to a urinary catheter system and included a balloon at an end of the catheter with a drainage port and an infusion port. A side port provided for inflation of the balloon where the balloon was inflated through a syringe or some like opening to pass the liquid through the port and expand the balloon in a radial direction. However, such prior art relied upon a balloon tip at the end of the catheter which essentially filled up the body cavity and necessitated additional flow passages for drainage and/or infusion of liquids.

Such prior art systems were cumbersome in nature and resulted in a substantially large diameter catheter tubular member which was inserted through orifices in the patient's body. Additionally, operating mechanisms were somewhat complex in that the maintenance of the retention member (which was the balloon) was based upon use of external mechanisms which were complex and took time to operate.

Other prior art catheter systems such as that disclosed in the Termanini U.S. Pat. No. 4,154,242 were directed particularly to bladder catheter devices where retention mechanisms were provided in the form of spring elements being used as wings which were expanded into a mushroom-like open contour. The spring-like wings were opened within the body cavity to an "open" position to maintain the catheter within the body cavity. However, such prior art, although having the springs covered by thin walls of the catheter tubing, could be punctured and cause possible infection in the patient.

Additionally, such prior art systems necessitated the use of a threaded member to actuate the expandable wings (springs) which increases the time needed to open and close the wings. This time extension may be a critical parameter during a procedure and thus is a disadvantage of such prior art systems.

Other prior art systems which used wing-like members to maintain the catheter within body cavities of a patient are exemplified by the Wallace reference, U.S. Pat. No. 2,649,092. However, although such catheter systems provided for wings which could be radially extended from a tubular section, such did not provide for a simple and easily maneuverable locking mechanism to permit the wings to be maintained in the "open" position and/or "closed" position.

Other prior art systems as exemplified by the Kohl U.S. Pat. No. 3,397,699 were directed to retaining catheters which have resiliently biased wing flanges. However, although such prior art catheter systems did include radially extensible wings, the releasable locking procedure does not provide for an easily maneuverable and manipulatable actuation mechanism for the extension and retraction of the wings. Such results in a more complex and time consuming operation which may be a critical factor.

Other prior art catheter systems such as that disclosed in the Hakki U.S. Pat. No. 5,569,219 shows a hollow elastomeric tubular member with inflatable stiffening and/or reinforcing members capable of being inflated with some type of fluid. However, such prior art systems require multiple lumens and the inflatable function is made more cumbersome in manufacture and is disadvantageous in having a circular cross-sectional area even when deformed.

A further prior art system is disclosed in the Hakky U.S. Pat. No. 7,264,609 which does not include a Foley type balloon at a proximal end, but does not provide for a reliable, simple, and easily manipulatable locking mechanism for the wing members in either an open or closed position.

In other prior art catheter systems, such as that shown in the Santomieri U.S. Pat. No. 3,938,530 reference, there is disclosed a retention type catheter which expands wings in a radial direction to maintain the catheter within a body cavity. However, such prior art systems necessitate a cumbersome mechanism for actuating the retaining mechanisms to expand and/or retract the wings. Additionally, such prior art systems do not provide for a releasable locking system which is actuated in a time optimization procedure.

None of the prior art systems provide for an activation mechanism which is located at a distal end of a flexible tubular member with the activation mechanism having a piston member slidably displaceable within a cylinder housing member to selectively displace the retaining mechanism into an "open" position and a "closed" position. Additionally, such prior art systems do not provide for a piston member to be selectively displaceable in a linear direction for displacing the retaining mechanism into an "open" and "closed" position where the wing members are extended in a radial direction with respect to the axial direction.

SUMMARY OF THE INVENTION

It is an object of the present invention to provide an indwelling catheter with a retaining mechanism, the state of which is easily controlled by a person administering the urinary procedure and which is safe for the patient.

It is a further object of the present invention to provide an indwelling catheter with an improved retaining mechanism at the proximal end which is easily actuated by a person administering the procedure with no need of a sterile syringe or a sterile fluid and which is sufficiently stiff for introduction inside urinary bladder without the need for a stylet or a catheter introducer.

The catheter of the present invention includes a tubular member defining a longitudinal channel extending between the proximal and distal ends thereof. The longitudinal channel is adapted for passage of bodily fluids therethrough. A retaining mechanism is located at the proximal end of the tubular member for insertion into a body cavity of a patient. An activation mechanism is positioned at the distal end of the tubular member. An actuation linkage extends within the longitudinal channel of the tubular member of the catheter and is operatively coupled to the retaining and activation mechanisms. This coupling enables the actuation linkage to actuate the retaining mechanism to assume either an "open" position in which the catheter is retained within in the body cavity of a patient or a "closed" position used for insertion and removal of the catheter.

The actuation linkage is formed as a stainless steel wire, nylon wire, Dacron wire, or a plastic wire, etc., and reciprocates within the longitudinal channel of the tubular member of the catheter under the control of the activation mechanism. When the actuation linkage wire is retracted towards the distal end of the tubular member, the retaining mechanism is transformed into the "open" position, and when the actuation linkage wire is moved towards the proximal end of the tubular member, the retaining mechanism is transitioned in the "closed" position.

There are several modifications of the retaining mechanism contemplated in the present urinary catheter. For example, the retaining mechanism may include a pair of slits extending from a tip of the catheter along the wall of the tubular member, which are transformable into "wings" extending radially from the walls of the tubular member and spanning a distance corresponding to the length of the slits formed in the walls of the tubular member at the proximal end thereof. The retaining mechanism may be modified to include additional slits and wings so long as the retaining mechanism may remain easily controlled and compatible with the additional features herein described.

When inserted into the body cavity of a patient, the retaining mechanism of the catheter is in the "closed" position. Once the catheter is situated within the body cavity, the retaining mechanism is transformed into the "open" position and the wings press against the walls of the patient's body cavity to hold the catheter in place within the body cavity. The flexible material (silicone rubber or Latex) of the tubular member makes the thus created wings of the retaining mechanism "user friendly" causing minimal irritation to the walls of the body cavity by contact with the wings. Additionally, the openings formed between the wings are quite large to permit full drainage of the fluid from a patient's body cavity and effective delivery of medication or irrigation fluid thereto when needed.

The activation mechanism of the subject catheter is applicable to the above-described retaining mechanism. The activation mechanism is positioned at the distal end of the tubular member and includes a piston member which is slideably displaceable within a cylinder housing member. The actuation linkage extends throughout the longitudinal channel of the catheter through the piston member where it is secured to the piston member at a lower end portion. The piston member may transition within the cylinder housing member between a first position and a second position to actuate the "closed" or "open" positions of the retaining mechanism, respectively.

When the piston member is in a first position, the front end of the piston member is abutting the proximal end of the cylinder housing member. This positioning, corresponding to the "closed" position of the retaining mechanism will allow a user to easily insert the catheter into the body cavity of a patient or similarly, to remove the catheter therefrom at the end of a procedure. When the piston member is in a second position, the front end of the piston member has been pulled downward to displace the tip of the piston member from the proximal end of the cylinder housing member.

In a preferred embodiment, the cylinder housing member has two slots (a first slot and a second slot) extending in a longitudinal direction along the surface thereof defining a "U"-shaped configuration. The piston member includes a first protuberance extending from a surface thereof which is correspondingly shaped to fit within the slots of the cylinder housing member. The piston member is rotatable about an axis for positioning the first protuberance within the first and second slots of the cylinder housing member.

As the piston member is transitioned between first and second positions it is guided by the first protuberance which slides along the first slot of the cylinder housing member. As the piston member is slid to a second position to actuate the "open" position of the retaining mechanism, the first protuberance is stopped by a stop member on the distal end of the cylinder housing member.

The activation mechanism includes a locking mechanism to lock the retaining mechanism into the "open" position. The piston member is rotated in a predetermined direction to reposition the first protuberance from the first slot to the second slot of the cylinder housing member. As the first protuberance of the piston member is situated within the second slot, it is locked into position by a second protuberance on the front edge of the stop member of the cylinder housing member.

When it is desired that the catheter assume its "closed" state, personnel administering the procedure may unlock the activation mechanism by rotating the piston member in the opposite direction to overcome the second protuberance on the stop member of the cylinder housing member and reposition the first protuberance from the second slot back to the first slot of the cylinder housing member. At this point, the retaining mechanism will assume its "closed" position and the catheter may be safely removed from the body cavity of a patient.

These and other features and advantages of the present invention will become apparent in view of the further detailed description if taken in conjunction with the accompanying Patent Drawings.

DESCRIPTION OF THE PREFERRED EMBODIMENTS

Figure 1:
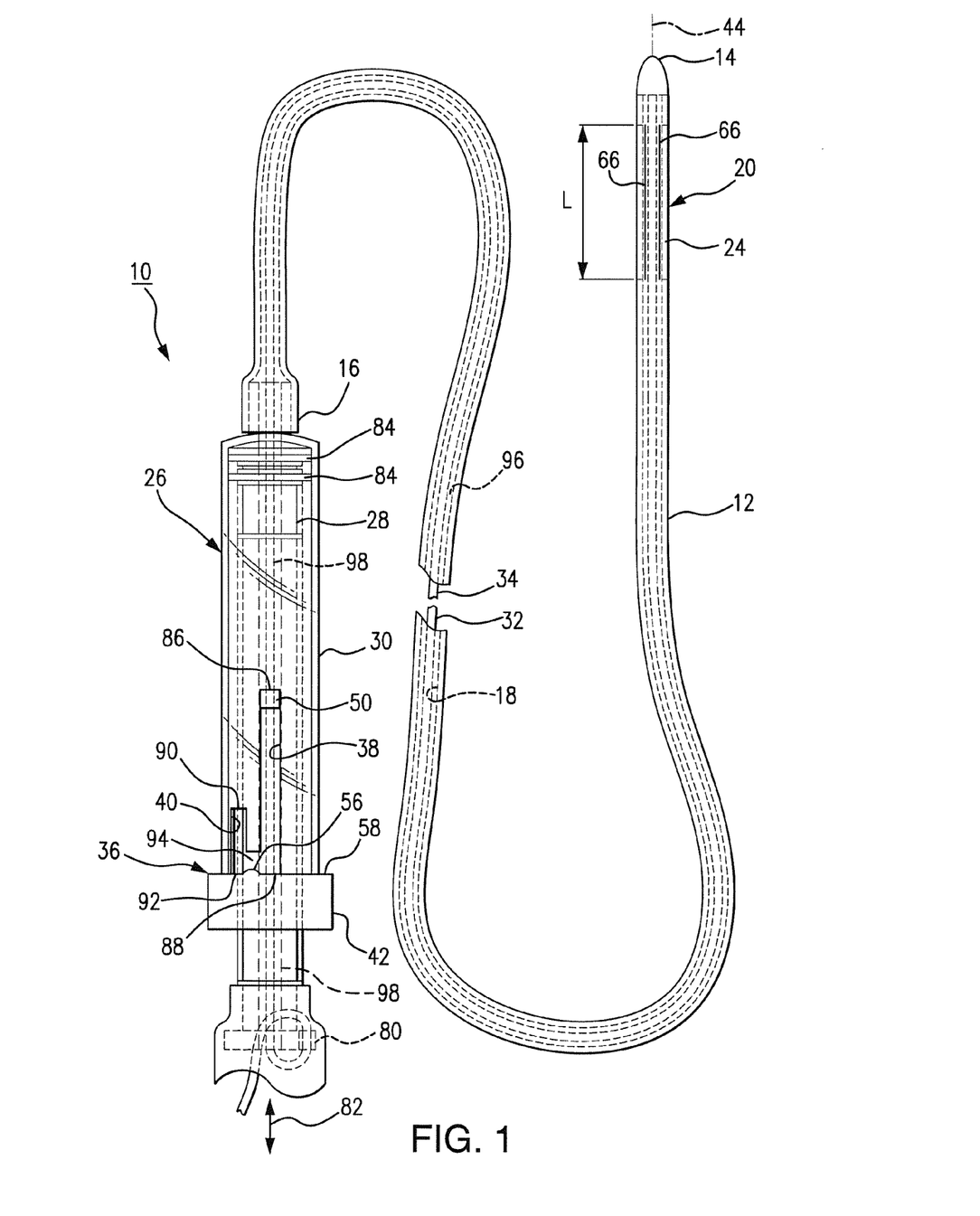
FIG. 1 is a schematic representation of the catheter of the present invention showing the retaining mechanism in its "closed" position.
Figure 2:
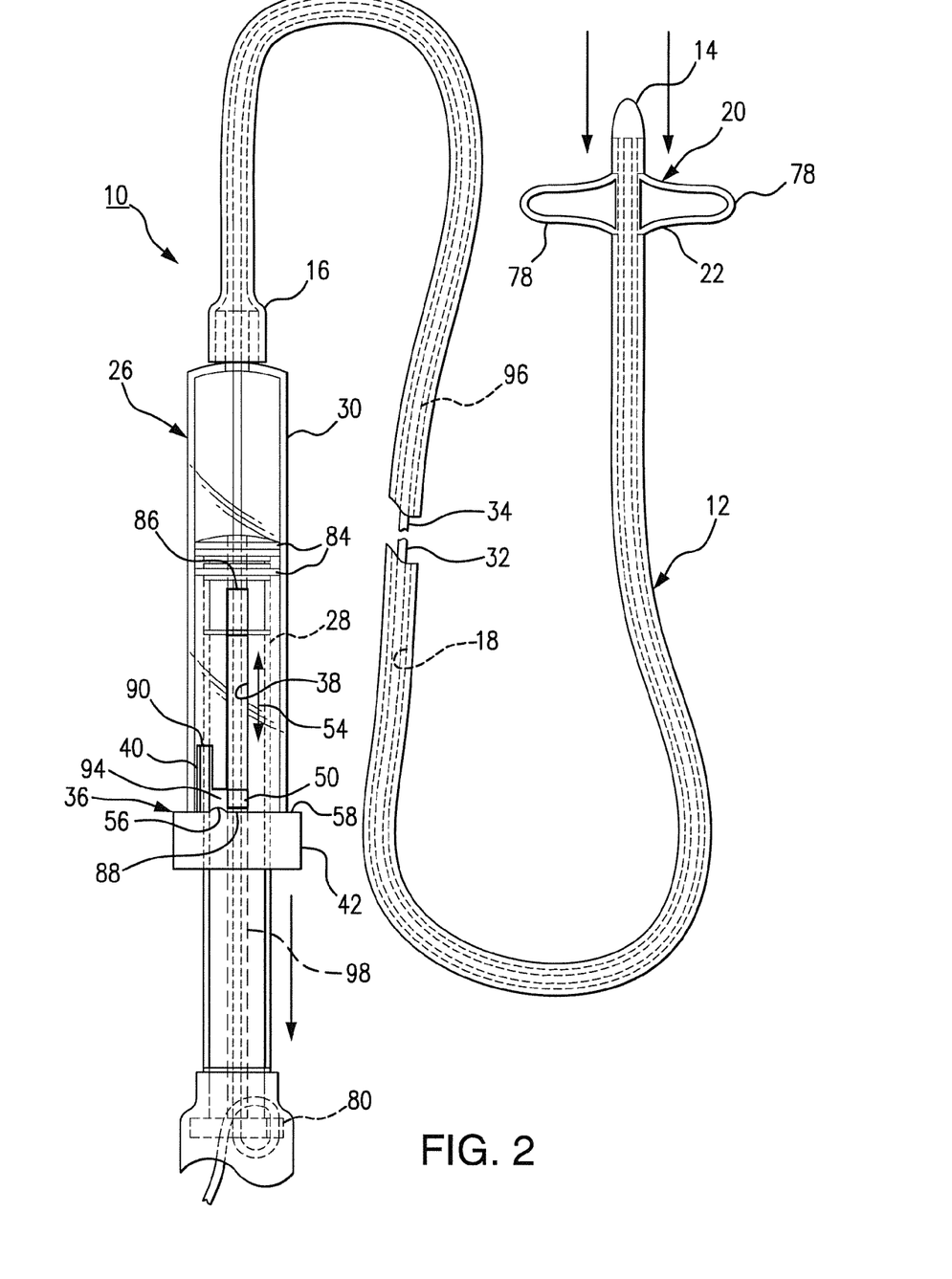
FIG. 2 is a schematic representation of the catheter of the present invention showing the retaining mechanism in its "open" position.
Figure 3:
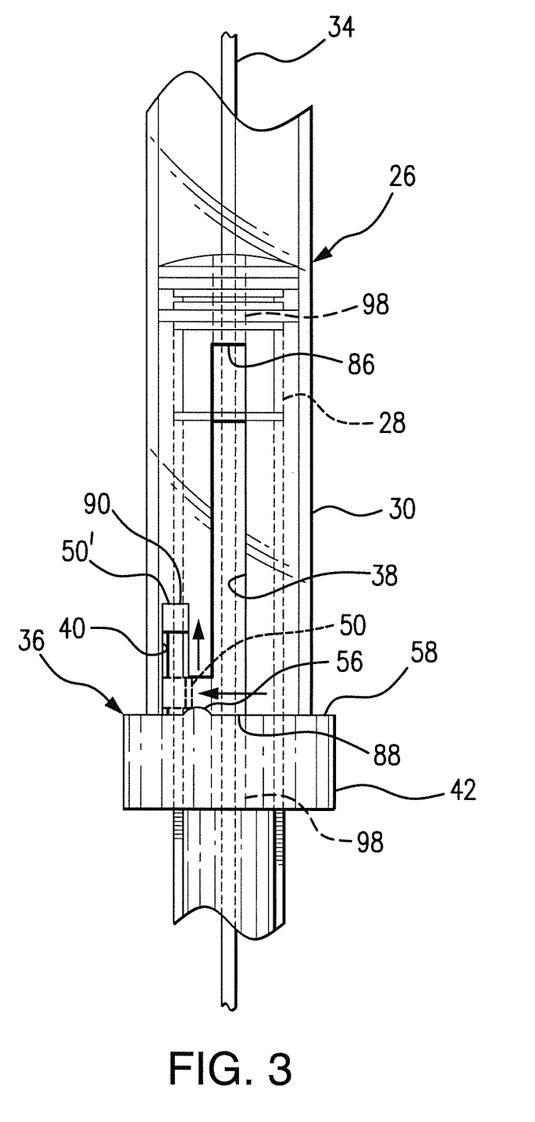
FIG. 3 shows the activation mechanism of the catheter of the present invention on a larger scale, illustrating direction of rotation as the first protuberance is moved from a first slot to a second slot of the cylinder housing member to "lock" the retaining mechanism into its "open" position.
Figure 4:
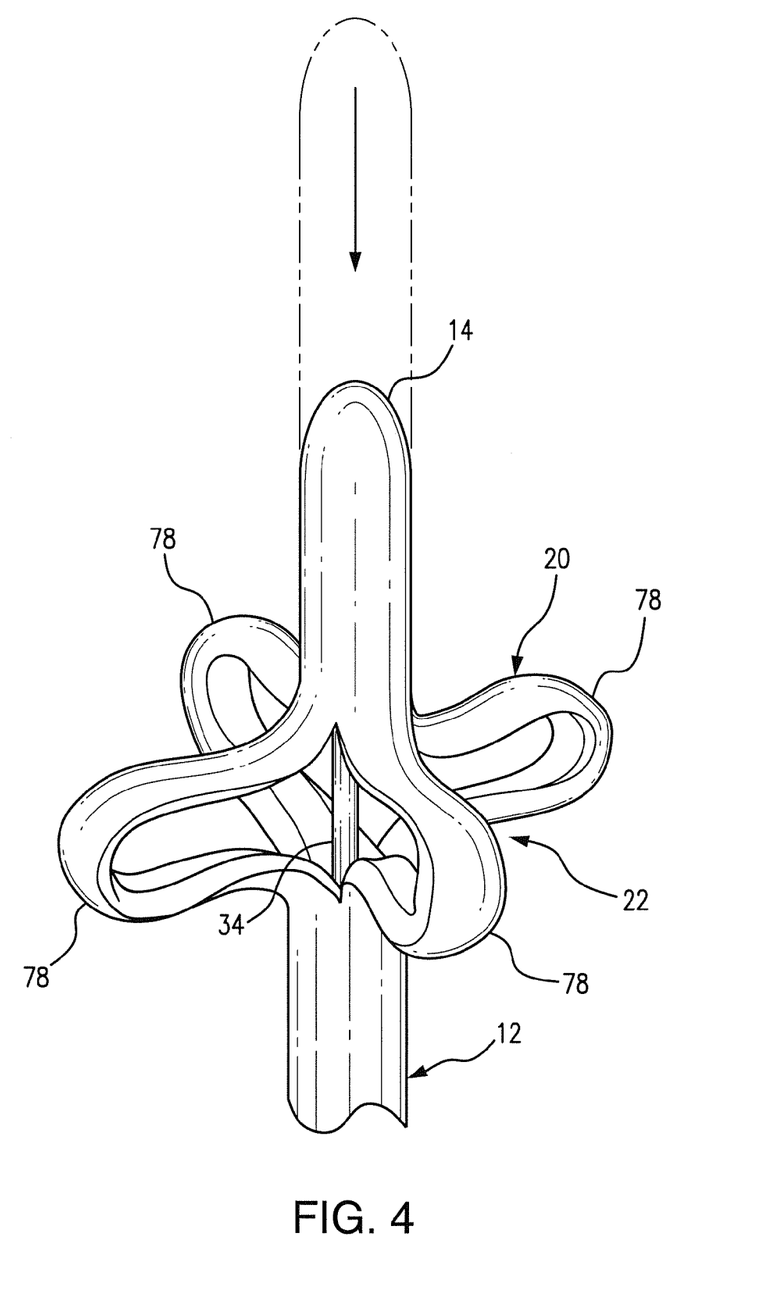
FIG. 4 is an enlarged view of the retaining mechanism of the present invention in its "open" position.

Referring now to FIGS. 1-4, there is catheter 10 adapted for insertion into a body cavity of a patient to permit passage of fluids therethrough and permit infusion and/or draining of the liquids from the body of the patient. In overall concept, catheter 10 includes a retaining mechanism 20 which can be displaced from a "closed" position as shown in FIG. 1 to an "open" position as shown in FIGS. 2 and 4. The "open" position is defined as the catheter prior to insertion of catheter 10 into the body of the patient as shown in FIG. 1. Once catheter 10 is inserted into the body cavity of the patient, catheter 10 can be operated to a position as shown in FIGS. 2 and 4 where catheter 10 is maintained in a relatively stable position within the body cavity of the patient.

The "closed" position of catheter 10 is shown in FIG. 1 where the tubular member 12 maintains a substantially constant diameter throughout its extended length between tubular member distal end 16 and tubular member proximal end 14. The "open" position is illustrated in FIGS. 2 and 4 where once catheter 10 has been inserted into the body cavity of the patient, wing members 78 may be expanded having an envelope diameter greater than the remaining outer diameter of tubular member 12. The envelope diameter of wing 78 are greater than the diameter of the remaining portions of tubular member 12 in order to block the removal of catheter 10 from the body cavity of the patient.

Retaining mechanism 20 is specifically adapted and designed for mounting and securement of catheter 10 within the body cavity of the patient during a procedure or at other times when fluids within the body cavity are being drained or fluids are being infused into the body cavity. In the manner indicated, retaining mechanism 20 maintains a relatively positionally stable condition of catheter 10 when such is maintained within the body cavity of the patient.

As previously discussed, and further will be described in following paragraphs, catheter 10 is inserted through passages within the human body into the body cavity of the patient in the "closed" position (FIG. 1) and then releasably locked into the "open" position shown in FIGS. 2 and 4 where the wings 78 are expanded to an envelope diameter greater than the diameter of the remaining portion of the tubular member. In this manner, movement of the patient will not dislodge catheter 10 from the body cavity of the patient and such provides a stable platform for the maintenance of catheter 10 within the body cavity of the patient.

Catheter 10 as seen in FIGS. 1-2 and 4 includes tubular member 12 which is flexible in composition and extends between tubular member proximal end 14 and tubular member distal end 16. Tubular member 12 is formed of a flexible composition such as rubber, various plastic compositions and/or polymers which permit flexibility of tubular member 12. The particular compositional nature of tubular member 12 is not important to the inventive concept as herein described with the exception that the composition permits sufficient flexibility to permit tortuous passage through passageways of the patient's body.

Tubular member 12 includes longitudinal channel 18 which extends from tubular member distal end 16 to a closed tubular member proximal end 14. Longitudinal direction 44 with respect to longitudinal channel 18 is defined as a center axis of tubular member 12. Thus, longitudinal direction 44 as depicted in FIG. 1 is not necessarily a linear direction but rather as defined in Applicant's subject system, is an axis line extension of tubular member 12. Thus, longitudinal direction 44 may be tortuous in contour and assume different linear type curvatures. Wire 32 extends through longitudinal channel 18 and the annular cross-section between wire 32 and the inner walls of the tubular member 12 form tubular member flow passageway 96 to permit infusion or draining of fluid therethrough.

Retaining mechanism 20 assumes two positions, either the "closed" position shown in FIG. 1 or the "open" position shown in FIGS. 2 and 4 dependent upon the activation of catheter 10. Retaining mechanism 20 is formed of a plurality of slits 66 which extend in longitudinal direction 44 through a length L as shown in FIG. 1. A plurality of slits are passed through the wall of tubular member 12 throughout the slit length L. There may be two or more slits 66 formed through the wall of tubular member 12 dependent upon the usage of catheter 10.

Once catheter 10 is actuated from the "closed" position in FIG. 1 to the "open" position in FIGS. 2 and 4, the slits 66 are transformed into wings 78 which provides for relatively stable positioning of catheter 10 within the body cavity of the patient. Since wings 78 are formed by slits 66 extending through length L through tubular member 12 for a predetermined distance, wings 78 are preferably formed integral with the tubular member 12. Wings 78 are formed of the same composition as tubular member 12, not important to the inventive concept as herein described with the exception that wings 78 be operable between the "closed" position shown in FIG. 1 to the "open" position shown in FIGS. 2 and 4 and vice versa.

Initially, in overall concept and in operation sequence, catheter 10 is in the "closed" position as shown in FIG. 1 and is inserted through an orifice in a patient's body and is passed or extended into the body cavity of interest within the patient. Wings 78 are radially displaced with respect to longitudinal direction 44 (radially displaced with respect to the axis line of tubular member 12) and through the operation of activation mechanism 26 and activation linkage 32 as will be described in following paragraphs. When wings 78 are displaced in the radial direction with respect to longitudinal direction 44, the catheter is maintained in a relatively stable position and a relatively releasably locked position within the patient's body cavity.

In this manner, retaining mechanism 20 of catheter 10 is insertable into the body cavity of the patient positioned in itself at the proximal end 14 of tubular member 12 with the retaining mechanism 20 being generally integral and unitarily formed of a tubular flexible material composition as has previously been described. In the manner to be further detailed in following paragraphs, retaining mechanism 20 is controllably and selectively actuated for assuming either the "open" position or "closed" position. Piston member 28 includes piston flow passageway 98 which is in fluid communication with tubular member flow passageway 96 to permit fluid being infused or drained to be infused or egressed from catheter 10. Piston flow passageway 98 extends throughout the length of piston member 28.

Catheter 10 further includes activation mechanism 26 positioned at tubular member distal end 16 of tubular member 12. Activation mechanism 26 includes piston member 28 which is slideably received and slideably displaceable within cylinder housing member 30 for selectively displacing retaining mechanism 20 into the "open" position and the "closed" position.

Activation mechanism 26 further includes a releasable locking mechanism 36 for selectively driving an actuation linkage 32 for selective displacement of retaining mechanism 20 to the "open" or "closed" position. As will be further detailed, locking mechanism 36 permits the releasable locking of retaining mechanism 20 in the "open" position when retaining mechanism 20 is positionally located within the body cavity of the patient and actuated for infusion or drainage of fluids.

Catheter 10 still further includes actuation linkage 32 which includes wire 34 extending from tubular member proximal end 14 of tubular member 12 through activation mechanism 26 to which it is secured. Wire 34 may be formed of a flexible composition such as plastic or other type composition compatible with the human body however the composition for wire 34 is not important to the inventive concept as herein described with the exception that it be sufficiently flexible to pass through tubular member longitudinal channel 18 in a tortuous manner.

Wire 34 is fixed to piston member 28 through a tie 80 formed on one end of piston member 28 and to an inner surface of tubular member 12 at the tubular member proximal end 14. Thus, wire 34 is fixedly mounted to a tip or end portion of tubular member 12 at tubular member proximal end 14 and secured in a fixed manner to piston member 28 on the other end as is clearly seen in FIGS. 1 and 2. The particular mode of tying of wire 34 to piston member 28 may be through a number of different modes which are not important to the inventive concept with the exception that wire 34 is fixedly attached to piston member 28 on one end and to the tip of tubular member 12 at the tubular proximal end 14.

In this manner when piston member 28 is displaced in axial direction 82, there is a displacement of tubular member proximal end 14 which permits radial displacement of wings 78. Since wire 34 extends through the longitudinal channel 18 and fixedly couples the retaining mechanism 20 and the activation mechanism 26 each to the other with the actuation linkage 32 reciprocally displaceable in the axial direction in a bi-directional manner relative to tubular member 12 and retaining mechanism 20 under control of the activation mechanism 26.

Activation mechanism 26 further includes cylinder housing member 30 generally formed of a relatively inflexible composition such as a closed cell plastic composition or some other like inflexible composition. Cylinder housing 30 may be transparent in order to allow viewing of the activation mechanism 26 during operational considerations.

Slots 38 and 40 as shown in FIGS. 1-3 are formed through a sidewall of cylinder housing member 30. First and second slots 38 and 40 extend in axial direction 82 as is seen in FIGS. 1-3. Both first and second slots 38 and 40 pass through the sidewall of cylinder housing member 30 and are formed into a U-shaped configuration and are in "open" communication each with respect to the other through communication passage or opening 94. Passageway 94 is the base of the overall U-shaped contour formed by slots 38 and 40 and passageway 94 provides for open communication between slots 38 and 40.

As will be further described in following paragraphs, the axial lengths of first and second slots 38 and 40 are not of equal length. As will be described, first slot 38 has an extended length in axial direction 82 which is greater than the axial length of second slot 40 to permit maintenance of wings 78 in an operable position when catheter 10 is in the "open" position.

First protuberance 50 is fitted to be slideably received in both first and second slots 38 and 40. First protuberance 50 extends in a radial direction from piston member 28 and is secured to a wall of piston member 28 that is generally formed integral therewith. First protuberance 50 extends above an outer wall surface of the cylinder housing member 30 to allow actuation and displacement of first protuberance 50 in axial direction 82 whether in first slot 38 or second slot 40. Thus, displacement of first protuberance 50 in axial direction 82 within either of first or second slots 38 and 40 causes a responsive displacement of piston member 28 within cylinder housing member 30.

As is seen in FIGS. 1 and 2, first protuberance 50 may be rotated from first slot 38 to second slot 40 in a reversible manner by rotation of piston member 28 about an axial line in axial direction 82 to provide a transference of first protuberance member 50 from one slot 38 to the second slot 40 or vice versa. Displacement of first protuberance 50 in axial direction 82 provides for operability of retaining mechanism 20 from a "closed" position to an "open" position or vice versa.

Stop member 42 is positionally located at a proximal end of cylinder housing member 30 and provides for a termination point in the displacement of first protuberance 50 when slideably operated within first and second slots 38 and 40. Stop member 42 is generally formed in one piece formation with respect to cylinder housing member 30 or may be a separate element which is fixedly attached to cylinder housing member 30. Stop member 42 is generally formed of an inflexible composition such as a closed cell plastic or some like composition. Stop member 42 includes front edge 58 which is a termination surface for the displacement of first protuberance 50 within either of first or second slots 38 and 40. First protuberance 50 extends in a radial direction through the wall of cylinder housing member 30 and can be actuated by the thumb of a user to displace first protuberance 50 in either of slots 38 or 40.

As has been stated, stop member 42 serves as a stopping or termination point for longitudinal or axial displacement of first protuberance 50 upon actuation by the user. First protuberance 50 is rotatable about axis line 82 of cylinder housing member 30 for positioning first protuberance 50 within first and/or second slots 38 and/or 40 of cylinder housing member 30. First protuberance 50 is thus slideably displaceable within first or second slots 38 and 40 when displaced in the direction defined by longitudinal slot direction arrow 54 shown in FIG. 2. First protuberance 50 may be releasably locked into alignment with either first or second slots 38 or 40.

Stop member 42 includes lug or second protuberance 56 which extends in axial direction 82 above stop member leading edge 58 and extends into communication passageway or channel 94 which provides open communication between first and second slots 38 and 40. Second protuberance 56 is configured to permit a force sliding of first protuberance 50 from first slot 38 to second slot 40 in a reversible manner but provide an impediment to the rotation where first protuberance 50 must forcibly be moved through communication channel 94. Thus, second protuberance or lug 56 provides for an impediment to the passage of first protuberance 50 from first to second slot 38 and 40 in a reversible manner. Second protuberance 56 is contoured to permit rotation of first protuberance 50 reversibly between slots 38 and 40 with a friction fitting which allows first protuberance 50 to be forced from one slot to the other slot 38 or 40.

In this manner, when catheter 10 is in a "closed" position as shown in FIG. 1, first protuberance 50 is positioned at a distal end of first slot 38. Subsequently, after insertion of catheter 10 and retaining mechanism 20 into the body cavity of the patient, first protuberance 50 may be displaced in axial direction 82 to the leading edge surface 58 of stop member 42. In this position, catheter 10 provides for the "open" position as shown in FIG. 2 where the wings 78 are extended in a radial direction with respect to tubular member 12. First protuberance 50 may then be forced through communication passage or channel 94 into alignment with second slot 40. Due to the fact that second slot 40 has a length less than the length of the first slot 38, first protuberance 50 may be displaced in axial direction 80 within second slot 40 without transferring or repositioning wings 78 into a "closed" position. Thus, when first protuberance 50 is within second slot 40 as is shown in FIG. 3, any displacement of first protuberance 50 within second slot 40 will not affect the "open" position of catheter 10 and retaining mechanism 20. Only by forcing first protuberance 50 through communication channel 94 into first slot 38 and a resultant displacement of first protuberance member 50 in axial direction 82 can the retaining mechanism 20 be collapsed to assume a "closed" position as shown in FIG. 1.

Piston member 28 may include retaining members in the form of O-rings 84 to permit a smooth displacement of piston member 28 within cylinder housing member 30. O-rings 84 may be formed of a rubber type composition and maintain stability of piston member 28 as piston member 28 is displaced in axial direction 82.

The subject concept is further directed to a method of operationally actuating catheter 10 within a patient's body cavity to permit catheter 10 to be operationally in an "open" position or a "closed" position as has previously been discussed. Initially, there is the establishment of a tubular member 12 having tubular member proximal end 14 and tubular member distal end 16. Tubular member 12 defines longitudinal channel 18 extending therethrough from tubular member proximal end 14 to tubular member distal end 16 with the tubular member distal end 16 being of a closed configuration. Longitudinal channel 18 extending through tubular member 12 permits bi-directional passage of fluids through tubular member 12. Retaining mechanism 20 is established and includes a plurality of slits 66 clearly shown in FIG. 1 in the "closed" position wherein when catheter 10 is operationally actuated, slits 66 expand into wings 78 as seen in FIG. 2. In this manner, retaining mechanism 20 is controllably and selectively displaceable to assume the "open" position (FIG. 2) and the "closed" position (FIG. 1). Retaining mechanism 20 is selectively displaced into the "open" position or the "closed" position by slideably displacing piston member 20 within cylinder housing member 30.

Activation of an actuation linkage 32 extending through the longitudinal channel 18 of the tubular member 12 permits displacement of the actuation linkage to operationally move the catheter 10 from the "open" position to the "closed" position and vice versa. The actuation linkage 32 couples retaining mechanism 20 and activation mechanism 26 each to the other. Retaining mechanism 20 is displaceable in a radial direction relative to longitudinal direction 44 defining an axis line of tubular member 12 in response to a displacement of piston member 28 in axial direction 82 as seen in FIG. 1.

Displacing of piston member 28 includes the step of displacing piston member 28 from a first position to a second position within cylinder housing member 30 to selectively displace retaining mechanism 20 to assume an "open" position. The displacement step of the piston member 28 further includes displacing piston member 28 from a second position to a first position within cylinder housing member 30 to selectively displace retaining mechanism 20 to assume the "closed" position. In this manner, first protuberance 50 being displaced in a bi-directional direction in accordance with direction line 54 creates a responsive displacement of piston member 28 in axial direction 82 which then causes wire 34 to be contracted or extended resulting in wings 78 being in the "open" position or the "closed" position.

The step of displacing piston member 28 further includes the step of sliding first protuberance 50 formed on a wall of the piston member 28 within first slot 38 formed through a wall of the cylinder housing member 30 in the bi-directional axial direction 82.

First protuberance 50 when bearing against first slot 38 first end 86 provides for catheter 10 to be in the "closed" position. When first protuberance 50 is displaced to first slot second end 88, retaining mechanism 20 is operatively displaced to the "open" position seen in FIG. 2.

Thus, the piston displacement step further includes the sliding of first protuberance 50 formed on a wall of piston member 28 within first slot 38 of cylinder housing member 30 in axial direction 82 to provide the "open" and "closed" conditions for catheter 10.

The activating step includes the locking step of retaining mechanism 20 into an "open" position where there is provided elongated second slot 40 in "open" communication with first slot 30 through channel 94. The locking step includes rotation of first protuberance 50 when it is adjacent second end 88 of first slot 38 into alignment with second slot 40 at second end 92 of second slot 40.

As has been previously discussed, second slot 40 and first slot 38 are of different axial lengths with the second slot 40 having a shorter length in the axial direction 82 than that of first slot 38. The length of second slot 40 is designed to permit displacement of first protuberance 50 throughout the length of second slot 40 without displacement of retaining mechanism 20 into a "closed" position. Thus, when first protuberance 50 is at any point in second slot 40 retaining mechanism 20 is maintained in the "open" position as seen in FIG. 2. Only by forceful displacement of first protuberance 50 through channel 94 into first slot 38 and then a further displacement of first protuberance 50 to upper end 86 of first slot 38 can catheter 10 be returned from the "open" position to the "closed" position as shown in FIG. 1.

Thus, the unequal lengths of first slot 38 and second slot 40 are designed such that a displacement of first protuberance 50 in second slot 40 does not provide for any displacement of wings 78 from the "open" position shown in FIG. 2.

Nub or second protuberance or lug 56 formed on a front edge of stop member 58 extends partially into open passageway 94 between first slot 38 and second slot 40 to provide an impediment to the rotational displacement of first protuberance 50 from first slot 38 to second slot 40 or vice versa. Nub or lug or second protuberance 56 provides for a type of frictional fit for first protuberance 50 when being rotated between first and second slots 38 and 40. In this manner, the user of catheter 10 can force protuberance 50 between first and second slots 38 and 40, however, once protuberance 50 is in one of the first or second slots 38 or 40, protuberance 50 is essentially releasably locked within the slot 38 or 40 and can only be moved in the axial direction 82 in free flow.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of the elements may be reversed or interposed, all without departing from the spirit or scope of the invention as defined in the appended claims.

What is claimed is:

1. A catheter, comprising:
   (a) a tubular member having a proximal end and a distal end, said tubular member defining a longitudinal channel extending between said proximal and distal ends, adapted for passage of fluids therethrough;
   (b) a retaining mechanism insertable in a body cavity of a patient and positioned at said proximal end of said tubular member, said retaining mechanism being integrally and unitarily formed in a one piece homogenous formation of a tubular flexible material controllably and selectively assuming an "open" position and a "closed" position;
   (c) an activation mechanism positioned at said distal end of said tubular member, said activation mechanism including a piston member linearly and reversibly slideably displaceable within a substantially transparent cylinder housing member for selectively displacing said retaining mechanism into said "open" position and said "closed" position, whereby viewing of withdrawn fluid is provided during operation; and
   (d) an actuation linkage comprising a wire extending through said longitudinal channel of said tubular member and coupling said retaining and activation mechanisms each to the other, said actuation linkage reciprocally displaceable in said longitudinal channel bi-directionally relative to said tubular member and said retaining mechanism under control of said activation mechanism, said wire extending throughout an entire length of said piston member and externally secured by a tie member to a fixed protuberance at a distal end thereof, whereby said wire may be adjusted in length by manipulation of said tie member.

2. The catheter as recited in claim 1, wherein said activation mechanism includes a locking mechanism for (1) selectively driving said actuation linkage to selectively displace said retaining mechanism to said "open" or "closed" position and (2) locking said retaining mechanism in said "open" position.

3. The catheter as recited in claim 2, wherein said cylinder housing member includes first slot and a second slot formed through a side wall of said cylinder housing member and a stop member is coupled to said cylinder housing.

4. The catheter as recited in claim 3, wherein said stop member is coupled to a distal end of said cylinder housing member.

5. The catheter as recited in claim 3, wherein said first and second slots extend in a longitudinal direction defined by an axis line of said cylinder housing member.

6. The catheter as recited in claim 3, wherein said first and second slots are formed in an open U-shaped configuration.

7. The catheter as recited in claim 3, wherein said stop member is a collar having a diameter greater than a diameter of said cylinder housing member.

8. The catheter as recited in claim 3, wherein said piston member has a first protuberance extending from a surface thereof, said first protuberance being rotatable about an axis line of said cylinder housing member for positioning said first protuberance within said first and second slots of said cylinder housing member.

9. The catheter as recited in claim 8, wherein said piston member is rotated to align said first protuberance with said second slot of said cylinder housing member to maintain said retaining mechanism in said "open" position.

10. The catheter as recited in claim 9, wherein said first protuberance is adjustable with said first or second slots and is locked into alignment with said first or second slots by a second protuberance extending from a front edge of said stop member.

11. The catheter as recited in claim 10, wherein said second protuberance is a lug member positioned between said first and second slots.

12. The catheter as recited in claim 8, wherein said piston member is rotated to align said first protuberance with said first slot and said second slot of said cylinder housing member such that said piston member is selectively displaceable in an axial direction to displace said retaining mechanism between said "open" and "closed" positions.

* * * * *